US005616138A

United States Patent [19]
Propp

[11] Patent Number: 5,616,138
[45] Date of Patent: Apr. 1, 1997

[54] URINE DRAINAGE AND COLLECTION DEVICE

[75] Inventor: Donald J. Propp, Dewitt, Mich.

[73] Assignee: Tri State Hospital Supply Corporation, Howell, Mich.

[21] Appl. No.: 520,761

[22] Filed: Aug. 29, 1995

[51] Int. Cl.$^6$ .............................. A61M 1/00; A61F 5/44; A61B 5/00
[52] U.S. Cl. .................... 604/317; 604/323; 604/324; 604/325; 604/349; 604/350; 128/760
[58] Field of Search .................................. 604/317–325, 604/349, 350, 283, 284, 83; 128/760, 761, 762, 764

[56] References Cited

U.S. PATENT DOCUMENTS

| | | |
|---|---|---|
| 3,601,119 | 8/1971 | Engelsher . |
| 3,608,552 | 9/1971 | Broerman ............................ 604/349 |
| 3,699,964 | 10/1972 | Ericson . |
| 3,906,935 | 9/1975 | Raia et al. . |
| 4,197,848 | 4/1980 | Garrett et al. . |
| 4,305,403 | 12/1981 | Dunn . |
| 4,500,311 | 2/1985 | Redmond et al. . |
| 4,805,635 | 2/1989 | Korf et al. . |
| 4,902,282 | 2/1990 | Bellotti et al. . |
| 5,053,003 | 10/1991 | Dadson et al. ...................... 604/283 |
| 5,207,661 | 5/1993 | Repschlager ........................ 604/317 |
| 5,211,642 | 5/1993 | Clendenning ....................... 604/317 |
| 5,251,639 | 10/1993 | Rentsch ............................... 128/761 |
| 5,395,347 | 3/1995 | Blecher et al. . |

FOREIGN PATENT DOCUMENTS 2193485  2/1988  United Kingdom .

*Primary Examiner*—John G. Weiss
*Assistant Examiner*—David J. Cho
*Attorney, Agent, or Firm*—Fildes & Outland, P.C.

[57] ABSTRACT

A urine drainage and collection device includes a tubing set having first, second, and third tube portions. Each tube portion has a first and second end. The first end of each tube portion is connected to and in communication with the first ends of the other two tube portions. A fluid metering device is connected to the second end of the second tube portion and permits introduction of fluid from the tubing set into the metering device. A receptacle in spaced fluid communication with the fluid metering device receives fluid from the metering device. An independent sampling device is in fluid communication with the second end of the third tube portion permits collection of fluid from the tubing set for sampling. A first flow control at an intermediate location of the second tube portion controls fluid flow through the second tube portion. A second flow control at an intermediate location of the spaced fluid communication between the metering device and receptacle controls fluid outflow from the metering device. A third flow control at an intermediate location of the of third tube portion controls fluid flow through the third tube portion, whereby fluid flow is selectively controllable for metering, draining and sampling fresh urine.

20 Claims, 1 Drawing Sheet

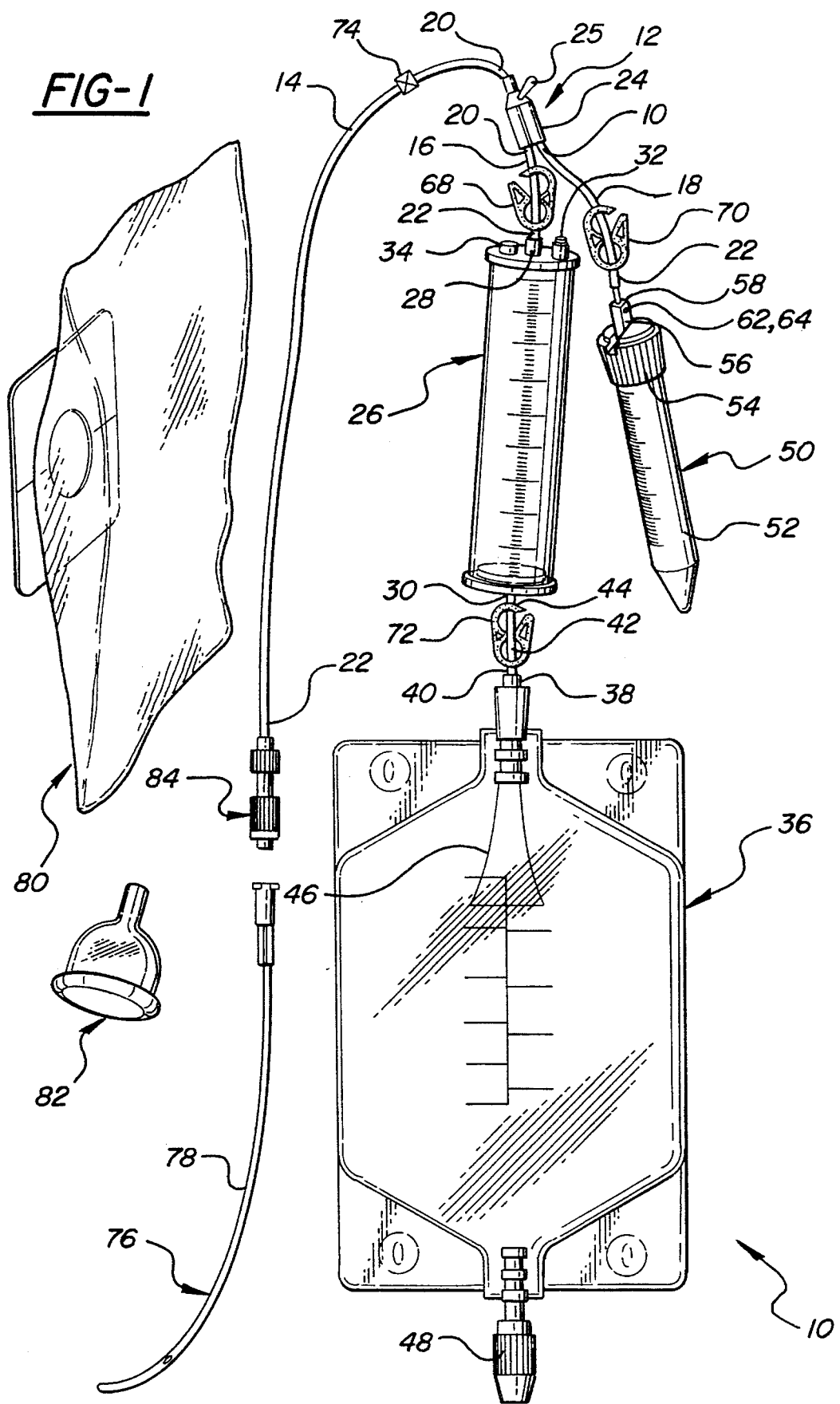

URINE DRAINAGE AND COLLECTION DEVICE

FIELD OF THE INVENTION

This invention relates to urinary catheterization and more particularly to a device that provides urological access, fluid measurement and drainage, as well as independent sampling of most recently produced urine.

BACKGROUND OF THE INVENTION

It is known in the art relating to urinary catheterization to perform such catheterization to drain a patient's bladder and to obtain most recent urine samples for laboratory analysis.

Known urine drainage systems often include a urinary catheter connected to a collection/drainage device. A catheter may be maintained in or on the patient for days or weeks. Samplings are typically taken from the collection device for laboratory analysis. It has long been a problem that the urine samples from the collection device are not the most recently produced urine. As a result, urine contained in the collection device has been known to become contaminated. This contaminated urine may produce unreliable laboratory analysis and unreliable biological test results. Therefore, in some known drainage systems, it is common to exchange the collection device for a sampling device when a urine sample is desired.

In these systems, this exchange involves interrupting the urine flow to the collection device, draining the collection device, removing the collection device from its communication with the catheter, connecting the sampling device in communication with the catheter, and establishing urine flow to the sampling device. After a urine sample is collected, in like fashion, the collection device must be exchanged for the sampling device. In addition to the exchange being a complicated procedure, the exchange of the collection device typically results in the spillage of urine and its contact with the patient or health care provider.

SUMMARY OF THE INVENTION

A feature of the present invention is a urine collection and drainage device that provides an integral independent fluid sampling device allowing selective urine collection for sampling to assure most recently produced uncontaminated urine for analysis and drainage without the need to exchange the urine collection device with the sampling device. The sample device is independent of and not in full, continuous communication with the urine drainage device providing a sterile receptacle for a urine sample.

The present invention also provides a metering device independent of the drainage and sampling devices for accurately measuring urine volume output versus time. Independent flow controls on tubes connecting the devices provide for convenience and low cost construction.

Accordingly, it is an object of this invention to simplify the procedures used for urine sampling, output measurement, and bladder drainage as well as eliminate the possibility of spilling urine during the shift in procedure from sampling to draining.

A more specific object of this invention is to provide a urine drainage and collection device including a tubing set having first, second, and third tube portions. Each tube portion has a first and second end. The first end of each tube portion is connected to and in flow communication with the first ends of the other two tube portions. The tubes are connected by a branch connector such as a Y or T-shaped bifurcation connector.

A fluid metering device including an inlet and an outlet is connected by its inlet to the second end of the second tube portion and permits the introduction of fluid from the tubing set into the metering device. A receptacle is fluidly connected in spaced relation to the outlet of the metering device to receive fluid from the independent metering device during draining.

A sampling device, independent of the metering device and receptacle and not in flow receiving communication therefrom, is removably connectable to the second end of the third tube portion. The sampling device permits collection in a sterile receptacle of most recently produced urine from the tubing set during sampling. A first flow control at an intermediate location on the second tube portion is operable to control fluid flow through the second tube portion. A second flow control at an intermediate location of the spaced fluid connection between the metering device and receptacle is operable to control outflow from the metering device. A third flow control at an intermediate location of the third tube portion is operable to control fluid flow through the third tube portion. Through operation of the first, second, and third flow controls, fluid is selectively communicable through the second and third tube portions for sampling or metering and draining.

A urological access device, such as an indwelling catheter, genitalia collection bag or external male condom catheter is fluidly connectable to the second end of the first tube portion to allow fluid to be introduced into the device.

These and other features and advantages of the invention will be more fully understood from the following detailed description of the invention taken together with the accompanying drawings.

BRIEF DESCRIPTION OF THE DRAWINGS

FIG. 1 is a perspective view of a urine drainage and collection device constructed in accordance with the present invention.

DETAILED DESCRIPTION OF THE INVENTION

Referring now to the drawing in detail, numeral 10 generally indicates a urine drainage and collection device including a tubing set 12 having a first, second, and third plastic tube portion, 14,16,18, respectively. Each tube portion 14,16,18 has a first and second end 20,22. The first end 20 of each tube portion 14,16,18 is connected to and in communication with the first ends of the other two tube portions. A branch connector shown as a bifurcation Y element 24 may be used to receive the first ends 20 of each of tube portions 14,16,18. Alternatively, a bifurcation T element, as is known, may be used to receive the first ends 20 of each of the tube portions 14,16,18. A mounting apparatus 25 is provided at this tube juncture for supporting the device 10 during use in a, generally, vertical hanging position allowing gravity fluid flow.

A fluid meter device 26, including an inlet end 28 and an outlet end 30, is connected to the second end 22 of the second tube portion 16. Fluid meter device 26 receives fluid from second tube portion 16 and is operable to meter the flow of urine as is more fully herein described. Preferably the fluid metering device 26 is a transparent chamber having graduations thereon for fluid output measurement. A preferable size range for the chamber 26 is 50 to 200 ml. Preferably, metering device 26 includes a hydrophobic vent 32 having a pore size range of 0.22 to 100 microns and a rubber septum sampling port 34. It is also preferable that the first and second tube 14,16 inside diameters are greater than the third tube 18 inside diameter to eliminate air lock flow obstruction at low bladder pressures.

A receptacle 36, such as a disposable, flexible, thin-walled plastic urinary drainage bag or other flow receptacle, is in fluid communication with the outlet end, 30 of the metering device 26. The receptacle 36 collects urine from the metering device 26 during draining of the patient's bladder continuously, or, if urine output is being measured, when clamp 72 is opened to dump the chamber 26 contents.

Drainage device 36 includes an inlet 38 connected to one end 40 of a fourth tube portion 42. The other end 44 of tube portion 42 is connected to the outlet end 30 of metering device 26. The inlet 38 may include a one-way valve 46 for preventing back flow of fluid and bacteria into the tubing set 12. Preferably, one-way valve 46 is an anti-reflux flap valve or other one-way flow control valve. Receptacle 36 includes an outlet 48 to permit drainage of urine from the receptacle. Outlet 48 has an open and closed position whereby in the open position the receptacle 36 can be drained, and in a closed position urine is collectable in receptacle 36. Preferably the drainage bag 36 is of a contents size range between 300 to 2,000 ml.

A sampling device 50 independent of the metering device 26 and receptacle 36 is connected to the second end 22 of the third tube portion 18. Sampling device 50 includes a collection vessel 52 such as a lab sampling centrifuge tube having a open end and a cap 54 in liquid sealing engagement with the tube open end. Cap 54 includes a spout 56 pivotally mounted on the cap for movement from an upright, opened position to a horizontal, closed position. Cap 54 is provided with an aperture which communicates with collection vessel 52 when the cap is secured on the collection vessel as is conventionally known.

Spout 56 is provided with an aperture 58 extending through the length of the spout so that when pivoted to the upright, opened position, the aperture is aligned and communicates with the aperture in the cap 54. When spout 56 is in the horizontal, closed position, the spout lies in the slot located in cap 54 and aperture 58 is no longer aligned with the aperture in the cap and there is no communication. Aperture 58 receives the end 22 of plastic tube portion 18 in frictional engagement, easily mounting the sampling device 50 to the tube portion 18. Alternatively, cap 54 is permanently retained on the second end 22 of plastic tube portion 18. Preferably, sampling device 50 is of a size range between 15 to 50 ml.

Spout 56 is also provided with a vent aperture 62 extending through the side of the spout so that when the spout is in the upright, opened position, the vent aperture is in communication with the aperture in the cap. Preferably, vent aperture 62 includes a hydrophobic vent filter 64. Vent aperture 62 vents the sampling device 50 during fluid collection for sampling as is readily apparent. In like fashion, when the spout 56 is in the horizontal closed position, the vent aperture 62 is no longer in communication with the aperture in the cap and sealed against leakage.

The second, third, and fourth tube portions 16,18,42 have flow controls defined by flow occluding clamps 68,70,72 mounted intermediate the ends 20,22 and 40,44 of the tube portions. Clamps 68,70,72 can be opened to allow the passage of fluid to the tube portions 16,18,42 and into the associated downstream device or closed to prohibit fluid flow through their associated tube portion.

In a preferred embodiment, the first tube portion 14 includes an anti-reflux valve 74. The inside diameters of the first and second tube portions 16,18 are greater than the inside diameter of the third tube portion 18.

A urological access device 76, such as a urethral indwelling catheter 78, genitalia covering collection bag 80, or external male condom catheter 82 is connected to the second end 22 of the first tube portion 14. The urological access device 76 provides bladder access for the drainage and collection device 10. Although the access device 78 is illustrated as being detachably connectable via a luer connector 84 to the first tube portion 14, the access device 76 can be non-removably bonded to the tube portion without fittings.

The present device 10 is typically provided as a preassembled sterile kit for continuous output catheterization for acute or chronic bladder drainage. Such a device is particularly well suited for neonatal care use. In such a system, the access device 78, 82 is applied to the patient to begin the catheterization or access device 80 is adhered to skin for genitalia bag method. Fluid received by the access device 78 or 82 is communicated through the tubing set 14. To take a urine sample, clamp 68 is closed and clamp 70 is opened to receive fresh urine in sampling device 50. When a sufficient sample has been received, clamp 70 is closed and clamp 68 is opened to allow the patient's bladder to drain. During draining, fluid is first received into metering device 26 and then, if clamp 72 is opened, into receptacle 36. During draining, clamp 72 can be closed to measure urine output of the patient.

Normally during draining, clamp 68 and 72 are in an opened position allowing fluid to be communicated from the access device 78 to the drainage device 36, and clamp 70 is in a closed position prohibiting the flow of urine to the second end 22 of the third tube portion 18. When urine samples for urinalysis is desired, sterile sampling device 50 is easily fitted to the second end 22 of the third tube portion 18 by insertion of the third tube portion through aperture 58 in the opened position spout 56. Alternatively, cap 54 may be left in place on tube 18 and a fresh collection vessel 52 substituted for the filled collection vessel. In this case, an extra non-spouted sealing cap can be used to seal the filled collection vessel 52.

Flow of only the most recently produced urine is directed to sampling device 50 by closing clamp 68 and opening clamp 70. When enough of a sample has been collected, clamp 70 is closed, the collection device 50 is removed from the second end 22 of the third tube portion 18, and the spout 56 is closed to seal the collected urine in the sampling device 50 for conveyance. Clamp 68 is opened and fluid is again directed into metering device 26 and drainage device 36. Alternatively, a fresh collection vessel 52 is connected to cap 54 after removal of a used collection vessel from the cap. An extra non-spouted sealing cap is put on the used collection vessel 52 for transit to a lab. When another sample is needed, the procedure is repeated with another sterile sampling device 50 or vessel 52. The most recently produced urine is easily sampled without the complications and possibility of urine contamination of heretofore systems.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A urine drainage and collection device comprising:

a tubing set having first, second, and third tube portions, each tube portion having a first and second end, the first end of each tube portion being connected to and in communication with the first ends of the other two tube portions;

a fluid metering device including an inlet and an outlet, said inlet being connected to the second end of said second tube portion allowing introduction of fluid from said tubing set into said metering device;

a receptacle in serial fluid communication with said fluid metering device outlet receiving fluid from said metering device;

a vented sampling device in fluid communication with said second end of said third tube portion allowing collection of fluid from said tubing set allowing sampling;

a first flow control at an intermediate location of said second tube portion to control fluid flow through said second tube portion;

a second flow control at an intermediate location between said metering device and receptacle to control fluid outflow from said metering device; and a third flow control at an intermediate location of said of third tube portion to control fluid flow through said third tube portion;

whereby through operation of said flow controls, gravity fluid flow is selectively controllable for metering, draining, and sampling fresh urine.

2. The device of claim 1 including a urological access device in fluid communication with said second end of said first tube portion for introducing fluid into said tubing set.

3. The device of claim 2 wherein said urological access device is a urethral indwelling catheter.

4. The device of claim 2 wherein said urological access device is a genitalia covering collection bag.

5. The device of claim 2 wherein said urological access device is an external male condom catheter.

6. The device of claim 1 wherein said first, second, and third flow controls are flow occluding clamps.

7. The device of claim 1 wherein said first tube portion second end includes at least one of a connector and an indwelling catheter.

8. The device of claim 1 wherein said second end of said first tube portion includes a connector.

9. The device of claim 1 wherein said first tube portion includes an anti-reflux valve between said first and second ends.

10. The device of claim 1 including a branch connector at the intersection of said first ends of said tube portions.

11. The device of claim 10 wherein said branch connector includes mounting apparatus for mounting said device.

12. The device of claim 1 wherein said metering device includes a hydrophobic vent.

13. The device of claim 1 wherein said metering device includes a septum sampling port.

14. The device of claim 1 wherein said receptacle is a urological drainage bag.

15. The device of claim 1 wherein said drainage bag includes an anti-reflux flap valve.

16. The device of claim 1 wherein said vented sampling device is a collection receptacle comprising:

a lab sampling tube having an open end; and a cap sealingly mountable on said tube open end;

said cap including a spout having an aperture therein for receiving said second end of said third tube portion for mounting said sampling device thereon and providing for flow communication with said tubing set;

said spout also including a vent for the passage of air out of said tube as fluid is received therein.

17. The device of claim 16 wherein said spout includes a hydrophobic vent filter.

18. The device of claim 11 wherein said first and second tube inside diameters are greater than said third tube inside diameter to eliminate air lock flow obstruction at low bladder pressures.

19. A urine drainage and collection device comprising:

fluid containment apparatus having a fluid inlet;

a fluid metering device including an inlet and an outlet, said inlet being in fluid communication with said containment apparatus;

a receptacle in serial fluid communication with said fluid metering device outlet receiving fluid from said metering device;

a vented sampling device in fluid communication with said fluid containment apparatus allowing collection of fluid from said containment apparatus allowing sampling;

a first flow control to control fluid flow into said metering device;

a second flow control at an intermediate location of said serial fluid communication between said metering device and receptacle to control fluid outflow from said metering device; and a third flow control to control fluid into said sampling device;

whereby through operation of said flow controls, gravity fluid flow is selectively controllable for metering, draining, and sampling fresh urine.

20. The device of claim 19 wherein said fluid containment apparatus is a tubing set having first, second, and third tube portions, each to a portion having a first and second end, the first end of each tube portion being connected to and in communication with the first ends of the other two tube portions.

* * * * *